United States Patent [19]

Deutsch

[11] 4,147,481

[45] Apr. 3, 1979

[54] ASYMMETRIC PERMEABLE MEMBER

[76] Inventor: Daniel H. Deutsch, 141 Kenworthy Dr., Pasadena, Calif. 91105

[21] Appl. No.: 826,270

[22] Filed: Aug. 19, 1977

[51] Int. Cl.² .............................................. F04B 39/00
[52] U.S. Cl. .................................................... 417/572
[58] Field of Search .................... 417/53, 207, 572; 73/23, 28

[56] References Cited

U.S. PATENT DOCUMENTS

| | | | |
|---|---|---|---|
| 3,150,818 | 9/1964 | Schumacher | 417/207 |
| 3,286,531 | 11/1966 | Shapiro et al. | 417/572 X |
| 3,565,551 | 2/1971 | Hobson | 417/53 X |
| 3,693,457 | 9/1972 | Pilat | 73/28 X |
| 3,795,135 | 3/1974 | Anderson | 73/28 |
| 3,837,762 | 9/1974 | Lee | 415/207 |

Primary Examiner—Carlton R. Croyle
Assistant Examiner—Edward Look
Attorney, Agent, or Firm—Edgar W. Averill, Jr.

[57] ABSTRACT

A sheet like member for causing the circulation of a gas therethrough. The asymmetric member has numerous shaped pores through it such that the absolute effusional resistance to gas flow is anisotropic. The member is useful in causing the circulation of gases.

125 Claims, 11 Drawing Figures

ASYMMETRIC PERMEABLE MEMBER

BACKGROUND OF THE DISCLOSURE

The circulation of fluids through open and closed systems has many applications in the arts, sciences and technology. Mechanical reciprocating pumps, centrifugal pumps, undulating tubes, thermal gradients and fans are all commonly used to move fluids. One particular application where the above listed circulating systems are often impractical is in bacteriological research where a sterile flask has a plug of cotton or other porous substance in the neck thereof and ambient air or other gas is allowed to pass through the cotton. For many reactions such as fermentation reactions the rate at which the air passes through the cotton is an important factor which determines the rate at which the reaction takes place.

A major shortcoming of the use of a cotton plug in the sterile shake flask is the very slow rate of gas exchange through the cotton plug. Consequently, the gas exchange through the cotton plug is rate limiting rather than the biological process in the bacteriological medium. Elaborate sterile gas pumping systems have been developed and used to increase the rate of air throughput. However, such systems are quite expensive, difficult to operate and maintain and provide a source of possible contamination. Some bacteriological processes are carried out under reduced pressure or elevated pressure and reactions are also carried out in the presence of a particular gas.

More particularly, the forced flow of gases has typically utilized mechanical compressors or other devices which can give rise to impurities caused by the necessary presence of lubricants. The need for moving gases in highly purified conditions has made most mechanical systems impractical. Furthermore, many gases are not compatible with the common materials of construction and thus can not be pumped by conventional devices. Still further, some processes require elevated temperatures or reduced temperatures. Systems for circulating air or other gases is made more difficult by the presence of such conditions.

SUMMARY OF THE INVENTION

It is the thus an object of the present invention to provide a gas circulating system which is simple to use, inexpensive to maintain and yet effective to increase the flow of gas through a conduit.

It is another important object of the present invention to provide a gas circulating system useful for depolluting industrial smoke stack gases.

It is a still further object of the present invention to provide a gas circulating system which consumes no energy.

The circulating system of the present invention comprises at least one sheet of a relatively impermeable material positionable within a gas impervious conduit and attachable in such a manner as to form a gas-tight seal across the conduit. The sheet has a thickness of less than about 3 millimeters and greater than about 0.001 microns. The sheet contains a plurality of tapered holes passing from one surface of the sheet to the other surface. A substantial majority of the holes are aligned so that they have their smaller openings on the first surface of the sheet and their larger openings on the second surface of the sheet. These holes may also be irregular and of a highly interconnected branched nature. The distance across the smaller openings is less than three times the mean free path of the molecules of the gas which is to be employed with the sheet. The sheet is both chemically and physically stable to the gas and of a relatively non-volatile nature under the conditions of temperature and pressure to be used. The mean absolute effusional resistance coefficient, $\xi$, is greater than $10^{-4}$ and less than 2.0 in the gas to be circulated, and when the sheet is positioned within a conduit to form a gas-tight seal across the conduit and the conduit is filled with the gas the gas is urged through the member and thusly through the conduit.

Some characteristics of the asymmetric gas-pervious members may be set forth by a series of equations set forth below wherein:

$R_i$ = the absolute effusional resistance of the member to the gas in the first direction, from side i of the member to side ii of the member (see FIG. 7 of the drawing discussed below).

T = the absolute temperature, °K., of the gas adjacent to the member.

$P_i$ = the pressure of the gas on side i of the member.

d = the thickness of the member.

A = the area of the member.

Q = the net gas flow rate through the member.

$R_{ii}$ = the absolute effusional resistance of the member to the gas in the second direction, from side ii of the member to side i of the member.

$P_{ii}$ = the pressure of the gas on side ii of the member.

When the gas pressure is set so that $P_i$ is the operating pressure on side "i" at T °K., and at the same time $P_{ii}$ is held near zero Torr so that $P_i$ is much greater than $P_{ii}$, $R_i$ is defined by Equation (1)

$$R_i = AP_i/Qd \qquad \text{Eq. (1)}$$

and correspondingly when the gas pressure is set so that $P_{ii}$ is the operating pressure on side ii at T °K., and at the same time $P_i$ is held near zero Torr so that $P_{ii}$ is much greater than $P_i$, $R_{ii}$ is defined by Equation (2).

$$R_{ii} = AP_{ii}/Qd \qquad \text{Eq. (2)}$$

When for a particular member with a given gas and at a temperature, T °K., if $R_i$ and $R_{ii}$, the absolute effusional resistance of the given member in the two opposite directions, as calculated from Equations (1) and (2) respectively are not equal under conditions where $P_i$ and $P_{ii}$ in Equations (1) and (2) respectively are equal, then the member's absolute effusional resistance is anisotropic for those specific operating conditions.

The member's mean absolute effusional resistance coefficient, $\xi$, is defined by Eq. (3)

$$\xi = \left| \frac{2(R_i - R_{ii})}{R_i + R_{ii}} \right| . \qquad \text{Eq. (3)}$$

and $\xi$ is a measure of the member's anistropy. For a given single asymmetric gas-pervious member and a given gas under specified temperature and pressure, the mean absolute effusional resistance coefficient $\xi$ must be greater than $10^{-4}$ and less than 2.0, in the gas to be circulated.

The tapered holes through the member are of such a size that the diameter of the openings of the holes at the smaller end are less than about three (3) times the mean free path of the molecules of the gas under the conditions employed and greater than the mean diameter of the molecules of the gas with approximately one tenth to one fiftieth of the mean free path of the gas molecules a typical useful range and where the gas molecules pass through the smaller end of the tapered holes by effusion.

As referred to herein the term "aerator" will be used to denote a gas circulating device which causes the flow of air or other gas through it.

DESCRIPTION OF THE PREFERRED EMBODIMENTS

Figures 1, 2:
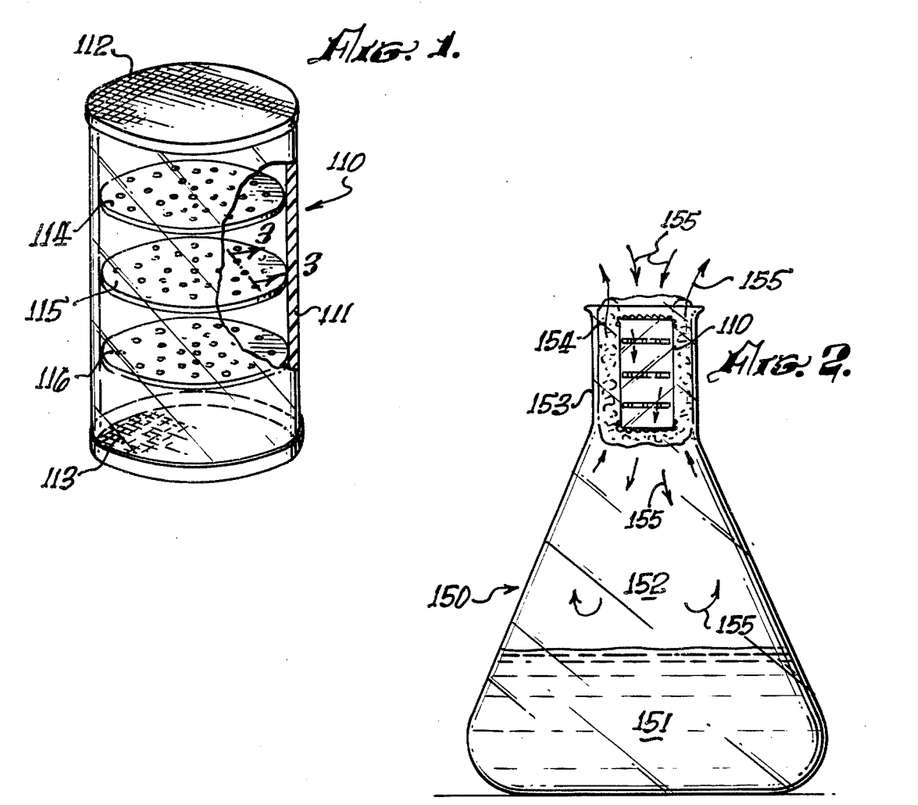
FIG. 1 is a perspective view, partially cut away, of the aerator of the present invention.
FIG. 2 is a side elevation showing the aerator of the present invention installed in the neck of the flask.

The aerator 110 of FIG. 1 is particularly adapted for use in the neck of a flask. Although numerous other uses of the aerator are possible, this application will serve to describe the aerator and is not to be considered a limitation on its possible use. Aerator 110 has cylindrical wall 111 which may be made from a glass tube or other hollow, member. A screen 112 may be positioned over the upper end of wall 111 and screen 113 is positioned over the lower end to protect the gas circulating members. Within wall 111 is a plurality of asymmetric gas pervious members 114, 115 and 116.

Figure 3:
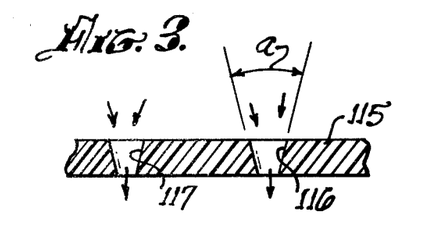
FIG. 3 is an enlarged cross-sectional view taken along the line 3—3 of FIG. 1.

As shown in FIG. 3, member 115 has a plurality of holes such as those indicated by reference character 116 and 117. Although the holes in member 115 are depicted as conical, the side wall of the holes may be convex or concave as viewed from the axis of the holes. Convex holes 120 and 121 are shown in member 122 of FIG. 4. These form generally conical holes which are flared at their larger openings. A substantial majority of the tapered holes are aligned so that their larger openings are on the same side of the member.

The size and shape of the holes form an important aspect of the present invention. When the end openings of the tapered holes are approximately circular, then the mean diameter of the smaller of the two openings must be less than three times as great as the mean free path of the molecules of the gas in which the aerator is to operate at the given temperature and pressure. When the opening of the holes is not circular, the important dimension is the shortest distance across the opening which passes through the center of the opening in the plane of the surface of the sheet. This dimension will be referred to herein as "the distance across the smaller opening". The mean free path of the molecules depends upon the composition, pressure and temperature of the gas and may be calculated by methods known to those skilled in the art. The "distance across the smaller opening" also must be greater than the minimum diameter of the given gas molecules. For air at 293° K. and 75 centimeters of mercury pressure, the mean free path of the molecules is about 0.09 microns. The "distance across the smaller opening" must therefore be less than 0.27 microns and greater than $3 \times 10^{-4}$ microns with $2 \times 10^{-3}$ microns being typical.

For pure oxygen at 293° K. at 7.5 centimeters of mercury pressure, the mean free path of oxygen molecules is about 1 micron. The "distance across the small opening" for an aerator for use under these conditions must be less than 3 microns and greater than $3 \times 10^{-4}$ microns. A typical diameter would be $2 \times 10^{-3}$ microns. For pure nitrogen at 278° K. and 0.75 centimeters of mercury, the mean free path is about 9 microns and the "distance across to the smaller opening" must be less than 27 microns and greater than $3 \times 10^{-4}$ microns with about $2 \times 10^{-3}$ microns being preferred. For helium at 293° K. and 7.5 centimeters of mercury pressure the mean free path is about 3 microns. The "distance across the smaller opening" must be less than 9 microns and greater than $2 \times 10^{-4}$ microns with $2 \times 10^{-3}$ microns being preferred. For hydrogen at 293° K. and 750 centimeters of mercury pressure the mean free path is 0.03 microns. The "distance across the smaller opening" must be less than 0.09 microns and greater than $2 \times 10^{-4}$ with $2 \times 10^{-3}$ microns being preferred dimension. For carbon dioxide at 293° K. at 750 centimeters of mercury pressure the mean free path is 0.006 microns. The "distance across the smaller opening" must be less than 0.018 microns and greater than $3 \times 10^{-4}$ microns with $4 \times 10^{-3}$ microns being preferred. For air at 203° K. and 7500 centimeters of mercury, the mean free path equals $9 \times 10^{-4}$ microns. The "distance across the smaller opening" must be less than $2.7 \times 10^{-3}$ microns and greater than $3 \times 10^{-4}$ microns with $6 \times 10^{-4}$ microns being preferred. In addition to the above mentioned gases the system is useful with a wide variety including but not limited to carbon dioxide, hydrogen, helium, argon sulphur dioxide, ammonia, monochlorotrifluoromethane, hexafluorocyclobutane, dichlorodifluormethane, tetrafluoromethane and water vapor or steam, and perhalogenated hydrocarbons.

Figure 4:
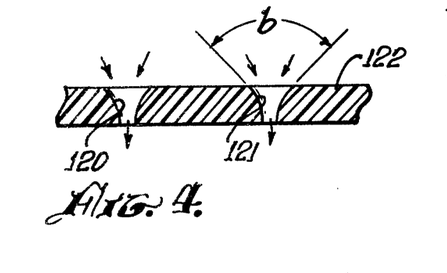
FIG. 4 is an enlarged cross-sectional view showing an alternate configuration of the openings of FIG. 3.

The angular dimension between the opposite sides of the conical hole indicated in FIG. 3 by reference character "a" should be between 2° and 150° with about 10° being preferred. When the opening is conical and in addition the larger opening is flared as shown by 121 in FIG. 4, the angle of the flare, indicated by reference character "b" should be between 10° and 180° with 150° being a preferred angular opening. While the exact angular dimension is not necessarily critical it is important that most of the openings on the upper side, as shown in FIG. 4, are larger than the openings on the lower side. With irregularly shaped holes it is difficult to quantify the size and shape and members containing irregularly shaped holes are best characterized by the member's mean absolute effusional resistance coefficient, $\xi$, for a specified gas at a given pressure and temperature.

The member thickness should be less than three millimeters with about 0.02 millimeters being preferred.

Member thickness such as 0.005 millimeters, 0.05 microns and as small as 0.001 microns are contemplated.

Figure 5:
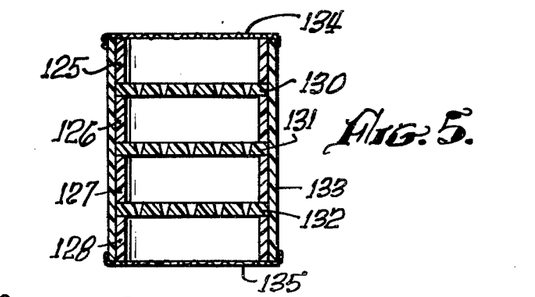
FIG. 5 is a cross-sectional side elevation of an alternate configuration of the aerator of FIG. 1.
Figure 6:
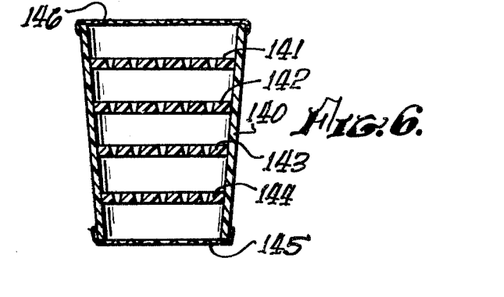
FIG. 6 is a cross-sectional side elevation of an alternate configuration of the aerator of FIG. 1.

The member may be glued, welded or otherwise affixed to the inner wall of the aerator conduit. Alternatively, as shown in FIG. 5, a plurality of spacers 125 through 128 hold members 130 through 132 in wall 133. Another method of holding the members within the wall is to provide a conical wall such as shown in FIG. 6 where frustro-conical wall 140 holds plates 141 through 144.

For use in the neck of a flask, the aerator is placed in the neck of flask 150 shown in FIG. 2. The reaction medium 151 is held in the flask and the air or other gas 152 is above the reaction medium 151. Aerator 110 is held in neck 153 of flask 150 by a wad of cotton 154. The direction of air flow is indicated by arrows 155. As shown by arrows 155 the gas passes downwardly through aerator 110 and upwardly through cotton wad 154. When used in this specific application, surrounded by a wad of cotton or similar material as in FIG. 2, screen 134 and 135 of FIG. 5; screen 145 and 146 of FIG. 6 and screens 112 and 113 of FIG. 1 may be used to protect the members.

The number of members utilized within the aerator may be varied considerably with one member having some effect and a larger number of members increasing the effectiveness of air flow. Generally, the effect of number of members is additive. For example, the aerator could have 1, 5, 87, 2340 members depending upon the desired effect. The aerator of the present invention will operate either quiescently or in a flask which is secured to a shaker table. Furthermore, the aerator may be inverted causing the air or gas to flow in the reverse direction.

The number of holes in any one member may be widely diverse depending upon the surroundings in which the member is to operate. A member having a single, tapered hole could be useful but generally a plurality of the holes is more useful. The number of holes should not, however, be such that adjacent holes intersect so that the geometry of the hole is destroyed. In other words, the number of holes should be such that there are actual holes although some limited overlapping is possible.

Referring to Equation (3) above, the mean absolute effusional resistance coefficient, $\xi$, should be greater than $1 \times 10^{-3}$ and preferably greater than $1 \times 10^{-4}$ and less than 2.0 in the gas to be circulated. A coefficient of about 0.1 is preferred for many practical applications. There are three different classes of openings which members of the present invention may utilize: First, idealized holes through a member, which is otherwise substantially impervious to the gas, where holes are identical in size and orientation. Such holes may be truncated pyramids where the cross section may be circular, eliptical, triangular, square, or polygonal. Secondly, the openings may be referred to as real holes where the holes are tapered and of distorted shape passing through a member which is otherwise substantially impervious to the gas. Thirdly, the member may be porous wherein the asymmetric holes through the member are both highly branched and forked with the generally smaller openings on the first surface of the member and the generally larger openings on the second surface of the member. Members may, of course, contain openings of any or all of the three above described types.

For may porous materials it is very difficult to measure the size of the openings on each side of the sheet since the openings can vary in both size and shape. Further, the holes through the member are not necessarily of simple and uniform dimensions. FIG. 7 depicts such a member with holes 150 and 151. This porous member as well as other gas pervious asymmetric members can be characterized most readily by the above-described absolute effusional resistances, $R_i$ and $R_{ii}$ along with $\xi$, the member's mean absolute effusional resistance coefficient. An isotropic, gas-pervious member is one where $\xi = 0$ and the degree of anisotropy may be judged by the magnitude of the coefficient, $\xi$.

Generally speaking, asymmetric pervious sheets which show anisotropic effusional gas resistance properties, that is $\xi$ is different from zero, may be prepared in either of two ways or a combination of these two ways:

(a) asymmetry is incorporated during the formation of the sheet itself as during the casting;
(b) the asymmetry is produced by modifying a symmetrical pervious sheet.

The later modification (b), may be carried out by one of two processes (c) or (d) or a combination of them:

(c) the symmetrical holes through the member are preferentially partially closed or filled on one side of the member in preference to the opposite side by electroplating, acylation, esterification, etherification, vapor deposition, sputtering, heat treating, bending, stretching, radiation treatment or other process;
(d) the symmetrical holes through the member are preferentially enlarged on one side of the member in preference to those on the opposite side by such processes as etching, leching, hydrolysis, electromachining, stretching, bending, heat treatment, radiation treatment, machining, punching, or by other processes.

Members may be made from sintered powders. When a compressed, finely-powdered solid is heated to a temperature somewhat below its melting point, the individual solid grains fuse together at their point of physical contact. This sintering, at the early stages, leaves large, interconnected voids and the mass is quite porous. As the temperature is increased or the time of heating is increased or both, the degree of sintering increases. The volume of the mass, upon increased sintering, decreases and the cross section of the void holes decreases in size.

Asymmetric sintered members may be prepared by different degrees of sintering on the two sides of the member such as would occur when the two sides were exposed to different sintering temperatures. If the starting powder was made up of particles of different sizes and the powder was classified by particle size across the member and then sintered, the side having the larger particles would have larger holes, the side with the smaller particles would have smaller holes, and inside the member holes would be of an intermediate size. Thus, generally tapered pores would be produced by such a classification of the particles prior to sintering. Such pores or openings may be highly interconnected and branched but the average mean diameter of the openings of the openings on the first surface are smaller than the average mean diameter on the second surface and the average mean diameter of the holes inside the member are of an intermediary average mean diameter. The material of the members is a gas impervious continuous phase.

A wide variety of materials can be used for fabrication of members. The material must be quite impermeable to gasses and must be chemically and physically stable to the gas with which it is to be employed. Plastics such as nylon and polyethylene; metals such as aluminum and iron, ceramics such as glass and other silicates and the like are useful with consideration of corrosion resistance, temperature limitations and the like being adjusted to the environment in which the members are to operate. The member should be non-volatile in the gaseous environment and the gas should be relatively insoluable in the member. By "relatively insoluable" it is intended to mean that the gas will not dissolve in the member to an extent sufficient to cause it to swell to an extent to weaken the member or to change the size or shape of the openings to an extent to impair their function.

Figure 7:
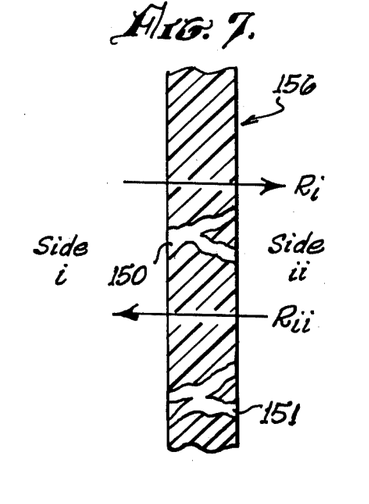
FIG. 7 is a cross-sectional side elevation of an aerator comprising an asymmetric porous sheet.

Equations 1 and 2 may be further understood by reference to FIG. 7 where member 156 has a first side referred to as side i in the drawing and a second side referred to as side ii. The absolute effusional resistance from side i to side ii is referred to both in Equation (1) and in the drawings by $R_i$ and the absolute effusional resistance in the reverse direction is referred to as $R_{ii}$. From $R_i$ and $R_{ii}$ the mean absolute effusional resistance coefficient, $\xi$, may be calculated as shown in Equation (3) above.

Member 156 may be fabricated from a wide variety of materials, such as polyethylene, polyporpylene, polyurethane, polycarbonates, nylon, polymethylmethacrylate, rubber, cellulose, modified celluloses, metals such as copper, iron, aluminum, zinc and tin; ceramics, minerals, and composites of various organic and inorganic materials.

Figure 8:
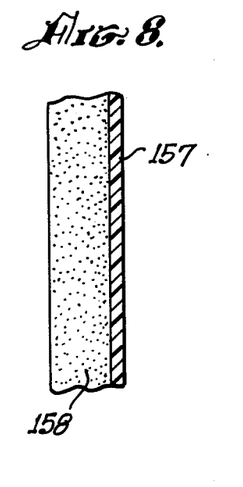
FIG. 8 is a cross-sectional side elevation of a singly supported asymmetric permeable sheet gas circulator.

Since the member may be very thin, it is appropriate in many instances that it be supported by an inert base. The base must permit the relatively free flow of the gas. As shown in FIG. 8, a coarse gas-porous base 158 is affixed to member 157. The support may be any inert, porous substance such as sintered glass. The member may be double supported as shown in FIG. 9 where member 160 is supported by bases 161 and 162.

While the use of the member of the present invention has been discussed as being particularly useful in the neck of the flask, the invention has far greater application. The member may be used in any conduit which is relatively gas impermeable. The member or members are positioned in a gas-impervious conduit and sealed around the edges so that the gas does not pass between the member and the conduit.

Figure 9:
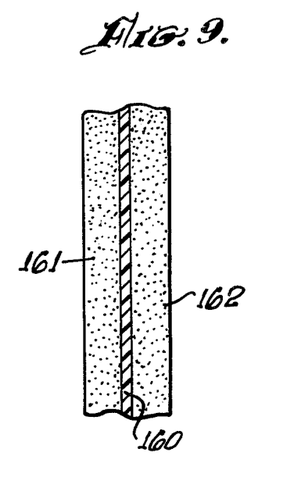
FIG. 9 is a cross-sectional side elevation of a doubly supported asymmetric permeable sheet gas circulator.
Figure 10:
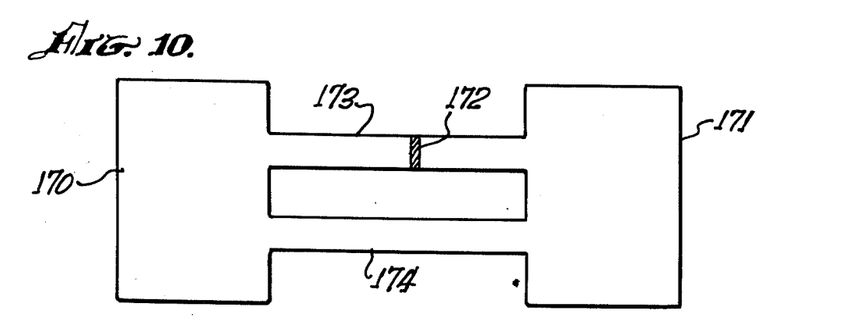
FIG. 10 is a side elevation of a pair of tanks connected by a pair of conduits, one of which contains a member of the present invention.

These asymmetric members as 156 in FIG. 7, 131 in FIG. 5, or 160 in FIG. 9 in which the mean absolute effusional resistance coefficient, $\xi$, is greater than $10^{-4}$ and less than 2.0 under certain specified conditions of gas composition, pressure and temperature, may be used for the circulation, of a gas between the tanks 170 and 171 in FIG. 10. Such a member is shown as 172 in FIG. 10 where it is sealed, gas tight, inside a conduit 173 connecting tanks 170 and 171. The conduit 174 provides for the return circulation. FIG. 10 shows the use of a single member. A plurality such as five members may be used in series in conduit 173 of FIG. 10. The number of members may be large such as 50, 300 or 2,500.

Figure 11:
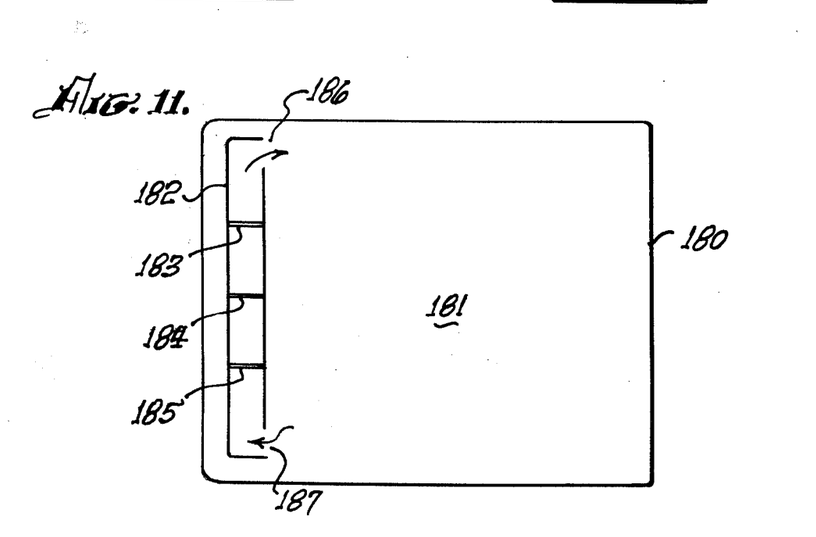
FIG. 11 is a side elevation of a room having a conduit containing a plurality of members of the present invention.

FIG. 11 illustrates how this device may be used as a circulator to induce circulation of air 181 or other gas in an enclosure such as a room or a tank 180. A conduit with gas impervious walls, 182 extends from top to bottom of the room 180. Affixed and sealed air tight thereto are three asymmetric members 183, 184 and 185 in which the mean absolute effusional resistance coefficient, $\xi$, is greater than $10^{-4}$ and less than 2.0, for air at ambient temperature and atmospheric pressure. These members, 183, 184 and 185 are all ordered in the same direction and all urge the circulation of the air upwardly in the direction of the arrows inwardly into entrance 187 and out of exit 186.

The present embodiments of this invention are thus to be considered in all respects as illustrative and not restrictive, the scope of the invention being indicated by the appended claims rather than by the foregoing description. All changes which come within the meaning and range of equivalency of the claims therefore are intended to be embraced therein.

I claim:
1. A gas circulating system comprising;
    at least one sheet of a relatively gas impermeable material positionable within a gas impervious conduit and attachable to said conduit in such a manner as to form a gas-tight seal across the conduit, and said sheet has a thickness of less than about 3 millimeters and greater than about 0.001 micron, and contains a multiplicity of tapered holes passing from one surface of the sheet to the other surface, wherein a substantial majority of the holes are aligned so that they have their smaller openings on the first surface of the sheet and their larger openings on the second surface of the sheet and wherein the distance across the smaller openings is less than three times the mean free path of the molecules of the gas which is to be employed with this gas circulating system and larger than the minimum diameter of such gas molecules, and wherein the sheet is both chemically and physically stable to the gas which is to be employed with this gas circulating system, and where the material of the sheet is relatively non-volatile under the conditions of temperature and gas pressure which are to be employed with this gas circulating system, and wherein the mean absolute effusional resistance coefficient, $\xi$, is greater than $10^{-4}$ and less than 2.0 and whereby when said sheet is positioned within a conduit to form a gas tight seal across the conduit and said conduit is filled with said gas, the gas is urged through said sheet and said conduit.
2. The circulating system of claim 1 wherein the tapered holes are uniform and the angular dimension between the opposite sides of the holes are between 2° and 150°.
3. The circulating system of claim 2 wherein said angle is about 10°.
4. The circulating system of claim 1 wherein said tapered holes are conical in shape.
5. The system of claim 1 wherein said system has one of said members.
6. The system of claim 1 wherein said system has a plurality of said members.
7. The system of claim 6 wherein said system has five of said members.
8. The system of claim 1 wherein the members of said system have a thickness of about 0.02 millimeters.
9. The system of claim 1 wherein the mean absolute effusional resistance coefficient, $\xi$, is approximately 0.1.
10. The system of claim 1 wherein said tapered holes are conical in shape and in addition flared at the end with the larger opening, wherein the angle between the opposite sides of the flare where it meets the surface of the member is between 10° and 180°.

11. The system of claim 10 wherein said angle is about 150°.

12. The system of claim 1 designed for use in air wherein the mean distance across the opening at the smaller end of the hole is about 0.002 microns.

13. The system of claim 1 wherein said member is supported by a coarse gas-pervious base on one side.

14. The system of claim 1 wherein said member is supported by a coarse gas-pervious base on both sides thereof.

15. The system of claim 13 wherein said coarse gas-pervious base is sintered glass.

16. The system of claim 14 wherein said coarse gas-pervious bases are sintered glass.

17. A gas circulating system comprising;
at least one member of a relatively gas impermeable material positionable within a gas impervious conduit and attachable to said conduit in such a manner as to form a gas-tight seal across the conduit, and said member has a thickness of less than about 3 millimeters and greater than about 0.001 micron, and contains a multiplicity of irregular, generally tapered holes passing from one surface of the member to the other surface, wherein a substantial majority of the holes are aligned so that they have their smaller openings on the first surface of the member and their larger openings on the second surface of the member and wherein the average mean distance across the smaller openings is less than three times the mean free path of the molecules of the gas which is to be employed with this gas circulating system and larger than the minimum diameter of such gas molecules, and wherein the member is both chemically and physically stable to the gas which is to be employed with this gas circulating system, and wherein the material of the member is relatively non-volatile under the conditions of temperature and gas pressure which are to be employed with this gas circulating system, and wherein the mean absolute effusional resistance coefficient, $\xi$, is greater than $10^{-4}$ and less than 2.0 in the gas to be circulated, and whereby when said member is positioned within a conduit to form a gas tight seal across the conduit and said conduit is filled with said gas, the gas is urged through said member and said conduit.

18. The circulating system of claim 17 wherein the irregular tapered holes are not uniform and the average mean value of the angular dimension between the opposite sides of the holes is between 2° and 150°.

19. The circulating system of claim 18 wherein the average mean value of the said angular dimension is about 10°.

20. The system of claim 17 wherein said system has one of said members.

21. The system of claim 17 wherein said system has a plurality of said members.

22. The system of claim 21 wherein said system has five of said members.

23. The system of claim 17 wherein the mean absolute effusional resistance coefficient, $\xi$, is approximately 0.1.

24. The system of claim 17 wherein said member has a thickness of about 0.02 millimeters.

25. The system of claim 17 wherein said irregular, generally tapered holes are in addition flared at the end with the larger opening wherein the average mean value of the angle between the opposite sides of the flare where the flare meets the surface of the member is between 10° and 180°.

26. The system of claim 25 wherein the average mean value of the said angle is about 150°.

27. The system of claim 17 designed for use with air wherein the mean distance across the opening at the smaller end of the hole is about 0.002 microns.

28. The system of claim 17 wherein said member has a thickness of about 0.002 millimeters.

29. The system of claim 17 wherein said member is supported by a coarse gas-pervious base on one side.

30. The system of claim 17 wherein said member is supported by a coarse gas-pervious base on both sides thereof.

31. The system of claim 29 wherein said coarse gas-pervious base is sintered glass.

32. The system of claim 30 wherein said coarse gas-pervious bases are sintered glass.

33. A gas circulating system comprising;
at least one member of a relatively gas impermeable material positionable within a gas impervious conduit and attachable in such a manner as to form a gas-tight seal across the conduit, and said member has a thickness of less than about 3 millimeters and greater than about 0.001 micron, and contains a multiplicity of highly interconnected and branched holes which pass from the first surface of the member to the second surface of the member, and wherein the average mean diameter of the openings of the holes on the first surface are smaller than the average mean diameter of the openings of the holes on the second surface and wherein the average mean diameter of the holes inside of the member are of an intermediary average mean diameter between the average mean diameters of the openings of the holes on the two opposite sides of the member, and wherein the solid material of the member consists of one relatively gas impervious continuous phase through which the network of holes pass, and wherein the average mean diameter of the openings of the holes in the first surface is greater than the average mean diameter of the molecules of the gas which is to be employed with this gas circulating system and less than three times the mean free path of the said gas molecules under the operating conditions of this gas circulating system, and wherein the mean absolute effusional resistance coefficient, $\xi$, is greater than $10^{-4}$ and less than 2.0 for the said member of this system when used with said gas, and wherein said member is both chemically and physically stable in the presence of said gas and wherein the material of the member is relatively non-volatile in the said gas to be used in conjunction with this gas circulating system, and whereby when said member is positioned within a conduit to form a gas-tight seal across the conduit, and said conduit is filled with said gas, the gas is urged through said member and said conduit.

34. The system of claim 33 wherein said system has one said members.

35. The system of claim 33 wherein said system has a plurality of said members.

36. The system of claim 35 wherein said system has five of said members.

37. The system of claim 33 wherein the members of said system have a thickness of about 0.02 millimeters.

38. The system of claim 33 wherein the mean absolute effusional resistance coefficient, $\xi$, is approximately 0.1.

39. The system of claim 33 designed for use in air wherein the average mean distance across the openings at the smaller end of the hole is about 0.002 microns.

40. The system of claim 33 wherein said member is supported by a coarse gas-pervious base on one side.

41. The system of claim 33 wherein said member is supported by a coarse gas-pervious base on both sides thereof.

42. The system of claim 40 wherein said coarse gas-pervious base is sintered glass.

43. The system of claim 41 wherein said coarse gas-pervious bases are sintered glass.

44. A gas circulating system comprising:
a gas;
at least one member of a relatively gas impermeable material positionable within a gas impervious conduit and attachable to said conduit in such a manner as to form a gas-tight seal across the conduit, and said sheet has a thickness of less than about 3 millimeters and greater than about 0.001 micron, and contains a multiplicity of tapered holes passing from one surface of the member to the other surface of the member, wherein a substantial majority of the holes are aligned so that they have their smaller openings on the first surface of the member and their larger openings on the second surface of the member and wherein the distance across the smaller opening is less than three times the mean free path of the gas employed in the gas circulating system and larger than the minimum diameter of said gas molecules and wherein the member is both chemically and physically stable to the said gas, and where the material of the member is relatively non-volatile under the conditions of temperature and gas pressure which are to be employed with this gas circulating system, and wherein the mean absolute effusional resistance coefficient, $\xi$, is greater than $10^{-4}$ and less than 2.0, and whereby when said member is positioned within a conduit to form a gas tight seal across the conduit and said conduit is filled with said gas, the gas is urged through said member and said conduit.

45. The circulating system of claim 44 wherein the tapered holes are uniform and the angular dimension between the opposite sides of the holes is between 2° and 150°.

46. The circulating system of claim 45 wherein said angle is about 10°.

47. The circulating system of claim 44 wherein said tapered holes are conical in shape.

48. The system of claim 44 wherein said system has one of said members.

49. The system of claim 44 wherein said system has a plurality of said members.

50. The system of claim 49 wherein said system has five of said members.

51. The system of claim 44 wherein the members of said system have a thickness of about 0.02 millimeters.

52. The system of claim 44 wherein the mean absolute effusional resistance coefficient, $\xi$, is approximately 0.1.

53. The system of claim 44 wherein said tapered holes are conical in shape and in addition flared at the end with the larger opening wherein the angle between the opposite sides of the flare where it meets the surface of the member is between 10° and 180°.

54. The system of claim 53 wherein said angle is about 150°.

55. The system of claim 44 designed for use in air wherein the mean distance across the opening at the smaller end of the holes is about 0.002 microns.

56. The system of claim 44 wherein said member is supported by a coarse gas-pervious base on one side.

57. The system of claim 44 wherein said member is supported by a coarse gas-pervious base on both sides thereof.

58. The system of claim 56 wherein said coarse gas-pervious base is sintered glass.

59. The system of claim 57 wherein said coarse gas-pervious bases are sintered glass.

60. The system of claim 44 wherein the gas is air.

61. The system of claim 44 wherein the gas is nitrogen.

62. The system of claim 44 wherein the gas is carbon dioxide.

63. The system of claim 44 wherein the gas is hydrogen.

64. The system of claim 44 wherein the gas is helium.

65. The system of claim 44 wherein the gas is argon.

66. The system of claim 44 wherein the gas is sulphur dioxide.

67. The system of claim 44 wherein the gas is a perhalogenated hydrocarbon.

68. The system of claim 67 wherein the gas is monochlorotrifluoromethane.

69. The system of claim 67 wherein the gas is hexafluorocyclobutane.

70. The system of claim 67 wherein the gas is dichlorodifluoromethane.

71. The system of claim 67 wherein the gas is tetrafluoromethane.

72. The system of claim 44 wherein the gas is water in the vapor state.

73. A gas circulating system comprising:
a gas;
at least one member of a relatively gas impermeable material positionable within a gas impervious conduit and attachable to said conduit in such a manner as to form a gas-tight seal across the conduit, and said member has a thickness of less than about 3 millimeters and greater than about 0.001 micron, and containing a multiplicity of irregular, generally tapered holes passing from one surface of the member to the other surface of the member, wherein a substantial majority of the holes are aligned so that they have their smaller openings on the first surface of the member and their larger openings on the second surface of the member and wherein the average mean distance across the smaller openings is less than three times the mean free path of the molecules of the gas employed in the gas circulating system and larger than the minimum diameter of said gas molecules, and wherein the member is both chemically and physically stable to said gas and wherein the material of said member is relatively non-volatile under the conditions of temperature and gas pressure which are to be employed with this gas circulating system, and wherein the mean absolute effusional resistance coefficient, $\xi$, is greater than $10^{-4}$ and less than 2.0 in the gas to be circulated and whereby when said member is positioned within a conduit to form a gas-tight seal across the conduit and said conduit is filled with said gas, the gas is urged through said chamber and said conduit.

74. The circulating system of claim 73 wherein the irregular tapered holes are not uniform and the average mean value of the angular dimension between the opposite sides of the holes is between 2° and 150°.

75. The circulating system of claim 74 wherein the average mean value of the said angular dimension is about 10°.

76. The system of claim 73 wherein said system has one of said members.

77. The system of claim 73 wherein said system has a plurality of said members.

78. The system of claim 77 wherein said system has five of said members.

79. The system of claim 73 wherein the mean absolute effusional resistance coefficient, $\xi$, is approximately 0.1.

80. The system of claim 73 wherein said member has a thickness of about 0.02 millimeters.

81. The system of claim 73 wherein said irregular, generally tapered holes are in addition flared at the end with the larger opening wherein the average mean value of the angle between the opposite sides of the flare where the flare meets the surface of the member is between 10° and 180°.

82. The system of claim 81 wherein the average mean value of the said angle is about 150°.

83. The system of claim 73 designed for use with air wherein the mean distance across the opening at the smaller end of the hole is about 0.002 microns.

84. The system of claim 73 wherein said member has a thickness of about 0.02 millimeters.

85. The system of claim 73 wherein said member is supported by a coarse gas-pervious base on one side.

86. The system of claim 73 wherein said member is supported by a coarse gas-pervious base on both sides thereof.

87. The system of claim 85 wherein said coarse gas-pervious base is sintered glass.

88. The system of claim 86 wherein said coarse gas-pervious bases are sintered glass.

89. The system of claim 73 wherein the gas is air.

90. The system of claim 73 wherein the gas is nitrogen.

91. The system of claim 73 wherein the gas is carbon dioxide.

92. The system of claim 73 wherein the gas is hydrogen.

93. The system of claim 73 wherein the gas is helium.

94. The system of claim 73 wherein the gas is argon.

95. The system of claim 73 wherein the gas is sulphur dioxide.

96. The system of claim 73 wherein the gas is a perhalogenated hydrocarbon.

97. The system of claim 73 wherein the gas is monochlorotrifluoromethane.

98. The system of claim 73 wherein the gas is hexafluorocyclobutane.

99. The system of claim 73 wherein the gas is dichlorodifluoromethane.

100. The system of claim 96 wherein the gas is tetrafluoromethane.

101. The system of claim 73 wherein the gas is water in the vapor state.

102. A gas circulating system comprising;
a gas;
at least one member of a relatively gas impermeable material, positionable within a gas impervious conduit and attachable in such a manner as to form a gas-tight seal across the conduit, and said member has a thickness of less than about 3 millimeters and greater than about 0.001 micron, and contains a multiplicity of highly inter-connected and branched holes which pass from the first surface of the member to the second surface of the member, and wherein the average mean diameter of the openings of the holes on the first surface are smaller than the average mean diameter of the openings of the holes on the second surface, and wherein the average mean diameter of the holes inside of the member are of an intermediary average mean diameter between the average mean diameter of the openings of the holes on the two opposite sides of the member, and wherein the solid material of the member consists of one relatively gas impervious continuous phase through which the network of holes pass, and wherein the average mean diameter of the openings of the holes in the first surface is greater than the average mean diameter of the molecules of the gas employed in the gas circulating system and less than three times the mean free path of the said gas molecules under the operating conditions of this gas circulating system, and wherein the mean absolute effusional resistance coefficient, $\xi$, is greater than $10^{-4}$ and less than 2.0 for said member and said gas of this system, and wherein said member is both chemically and physically stable in the presence of said gas, and wherein the material of said member is relatively non-volatile in the said gas at the temperature and pressure employed, and whereby when said member is positioned within a conduit to form a gas-tight seal across the conduit and said conduit is filled with said gas, the gas is urged through said member and said conduit.

103. The system of claim 102 wherein said system has one said members.

104. The system of claim 102 wherein said system has a plurality of said members.

105. The system of claim 104 wherein said system has five of said members.

106. The system of claim 102 wherein the members of said system have a thickness of about 0.02 millimeters.

107. The system of claim 102 wherein the mean absolute effusional resistance coefficient, $\xi$, is approximately 0.1.

108. The system of claim 102 designed for use in air wherein the average mean distance across the openings at the smaller end of the hole is about 0.002 microns.

109. The system of claim 102 wherein said member is supported by a coarse gas-pervious base on one side.

110. The system of claim 102 wherein said member is supported by a coarse gas-pervious base on both sides thereof.

111. The system of claim 109 wherein said coarse gas-pervious bas is sintered glass.

112. The system of claim 110 wherein said coarse gas-pervious bases are sintered glass.

113. The system of claim 102 wherein the gas is air.

114. The system of claim 102 wherein the gas is nitrogen.

115. The system of claim 102 wherein the gas is carbon dioxide.

116. The system of claim 102 wherein the gas is hydrogen.

117. The system of claim 102 wherein the gas is helium.

118. The system of claim 102 wherein the gas is argon.

119. The system of claim 102 wherein the gas is sulphur dioxide.

120. The system of claim 102 wherein the gas is a perhalogenated hydrocarbon.

121. The system of claim 120 wherein the gas is monochlorotrifluoromethane.

122. The system of claim 120 wherein the gas is hexafluorocyclobutane.

123. The system of claim 120 wherein the gas is dichlorodifluoromethane.

124. The system of claim 120 wherein the gas is tetrafluoromethane.

125. The system of claim 102 wherein the gas is water in the vapor state.

* * * * *